United States Patent [19]

Miyata et al.

[11] Patent Number: 4,962,746
[45] Date of Patent: Oct. 16, 1990

[54] MIXING LIQUID RATIO DETECTOR DEVICE

[75] Inventors: Shigeru Miyata; Kiyotaka Ohno, both of Nagoya, Japan

[73] Assignee: NGK Spark Plug Co., Ltd., Nagoya, Japan

[21] Appl. No.: 438,513

[22] Filed: Nov. 17, 1989

[30] Foreign Application Priority Data

Nov. 23, 1988 [JP] Japan ............................... 63-295478
Feb. 20, 1989 [JP] Japan ............................... 1-40008

[51] Int. Cl.$^5$ .......................... F02P 9/00; F02B 75/12; G01M 21/00
[52] U.S. Cl. .................................... 123/613; 123/117; 356/436
[58] Field of Search ....................... 123/613, 117, 494; 356/436, 437

[56] References Cited

U.S. PATENT DOCUMENTS

| | | | |
|---|---|---|---|
| 4,116,174 | 9/1978 | Schuchting | 123/613 |
| 4,770,129 | 9/1988 | Miyata et al. | 123/49 X |
| 4,794,266 | 12/1988 | Saar | 356/437 |
| 4,821,700 | 4/1989 | Webler et al. | 123/49 X |
| 4,843,248 | 6/1989 | Miyata et al. | 356/436 |
| 4,898,462 | 2/1990 | Numata et al. | 356/436 |
| 4,905,655 | 3/1990 | Mackawa | 123/49 X |

Primary Examiner—Raymond A. Nelli
Attorney, Agent, or Firm—Cooper & Dunham

[57] ABSTRACT

In a mixing liquid ratio detector device, a LED and a photo diode are provided in a manner to sandwich an optically permeable column. The light emitting area of the LED and the light receiving area of the photo diode are each arranged in the neighborhood of the column in generally perpendicular relationship with a boundary between a mixing liquid and the column, such that light beams from the LED enter the boundary through one side of the column, the light beams incident on the boundary at an angle more than a critical angle being totally reflected from the boundary, and advancing through an inner portion of the column to come out from the other side of the column, and impinging on the photo diode.

3 Claims, 7 Drawing Sheets

Fig. 4
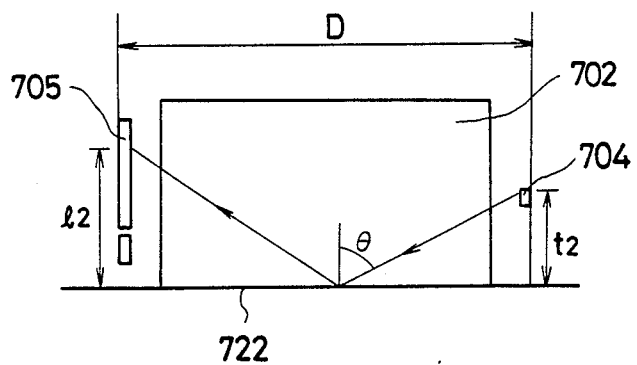
Fig. 5a  Counterpart Device
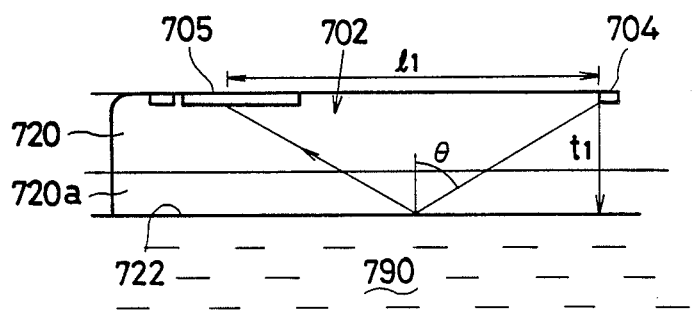

Fig. 5 Counterpart Device

MIXING LIQUID RATIO DETECTOR DEVICE

BACKGROUND OF THE INVENTION

1. Field of the Invention

This invention relates to a liquid mixing sensor which optically detects mixing ratio of a mixing liquid which includes at least two kinds of liquid components.

2. Description of Prior Art

In an internal engine of automobile, mixing fuel of gasoline and alcohol has been employed these days as a substitute of gasoline.

The substitute fuel forces to equip detector device which continuously detects mixing ratio of gasoline and alcohol to obtain an appropriate air-fuel ratio.

As seen in FIG. 5a, a counterpart detector device has an optically permeable member 720a, a bottom surface 722 of which is brought in contact with a mixing liquid 790 composed of gasoline and alcohol.

The member 702a is enclosed into a casing in which an epoxy mould resin 720 is filled to form an optically permeable column 702. A LED 704 and a photo diode 705 are embedded into the epoxy mould resin 720 in parallel relationship with the bottom surface 722.

Light beams from the LED 704 advance into an inner portion of the column 702 to be incident on the bottom surface 722 at more than a critical angle, and totally reflecting from the bottom surface 722 so as to impinge on the photo diode 705 which produces an output according to the intensity of the light beams impinged.

In this counterpart device, however, it is necessary to increase light receiving area of the photo diode due to increased incident angle on the column 702, and at the same time, it is necessary to determine greater distance between the photodiode 705 and the LED 704 so as to make scale of the device larger as a whole.

In addition, since it is necessary that the photo diode 705 and the LED 704 are each located in the mould resin 720, it is difficult to mould resin which has characteristics satisfactory for all the factors such as adhesion, expansion, refraction, transparency and endurance.

Therefore, it is an object of the invention to provide a detector device which last for long period of servicing time with low cost, small scale and high precision.

According to the invention, there is provided a mixing liquid ratio detector device comprising;

an optically permeable column, a bottom surface of which is brought in contact with a mixing liquid computerized of at least two components, and forming a boundary between the mixing liquid and the bottom surface which is brought in contact with a mixing liquid;

a light emitting element located to face to one side of the optically permeable column;

a light receiving element located in the opposite relationship with the light emitting element in a manner to face to another side of the column with the column interposed therebetween;

light receiving area of the light receiving element and light emitting area of the light emitting element being each arranged in the neighborhood of the column in generally perpendicular relationship with the boundary between the mixing liquid and the column, such that light beams from the light emitting element enter the boundary through one side of the column, the light beams incident on the boundary at an angle more than a critical angle being totally reflected from the boundary, and advancing through an inner portion of the column to come out from the other side of the column, and impinging on the light receiving element so as to produce an output according to the intensity of the light beams impinged thereon.

Further, another example of this kind of detector device (D) is shown in FIG. 5 as a kind of counterpart device.

This counterpart device carries a triangle prism 200 disposed to have a boundary with a mixing fuel 110. A LED (light emitting diode) 300 and a photo diode 400 are placed at both sides of the prism 200.

However, the detector device (D) has the following drawbacks.

The triangle prism is costly with insufficient compensation which is required due to temperature and deterioration of the LED, thus leading to avoiding high precision measurement.

Even recently introduced detector device has following drawbacks.

The height of optical permeable column increases to make difficult to be light weight. Light receiving area of the photo diode increases because broad range is required in which the light beams impinge on the photo diode.

Therefore, the invention has its object to provide a mixing liquid ratio detector device which is capable of eliminating all the drawbacks mentioned above, enabling to provide a mixing liquid ratio detector device which enables to accurately detect mixing ratio with lightweight column and small-scaled light receiving element because light receiving and light emitting diode are integrated by a gel-like filler.

According to the invention there is provided a liquid mixing ratio detector device comprising;

an optically permeable column, a bottom surface of which is brought in contact with a mixing liquid composed of at least two components, and forming a boundary between the mixing liquid and the bottom surface which is brought in contact with the mixing liquid;

a holder disposed for supporting the optically permeable column;

a light emitting element located to face to one side of the optically permeable column;

a light receiving element located in the opposite side to the light emitting element with the column interposed therebetween;

a transparent liquid filler disposed to fill between the light emitting element and the column, and at the same time, filling between the light receiving element and the column;

an arrangement between height and diametrical dimension of the column, and vertical position of the light receiving element being determined such that light beams from the light emitting element enter into one side of the column through the transparent liquid filler to be incident on the boundary, the light beams totally reflect from the boundary advance through inner portion of the column to come out partly from the other side of the column, and partly coming out from an upper surface of the column to impinge on the light receiving element so as to produce an output according to the light beams impinged.

It becomes unnecessary to make all the light beams from the boundary come out from the other side of the column, thus enabling to reduce axial dimension of the column.

On the other hand, the transparent liquid filler is determined to be smaller than the column in refraction index, thus controlling dispersion of the light beams which impinge on the light receiving element.

It is because of preventing the light beams from reflecting at the upper surface of the column that all the light beams incident on the boundary at more than a critical angle are adapted to come out from the other side of the column.

BRIEF DESCRIPTION OF THE DRAWINGS

FIG. 4 is a schematic view depicted for the purpose of explaining operation;

FIG. 5a is a schematic view of other counterpart detector device depicted for the purpose comparing it to the device according to present invention;

DETAILED DESCRIPTION OF THE INVENTION

Figure 1:
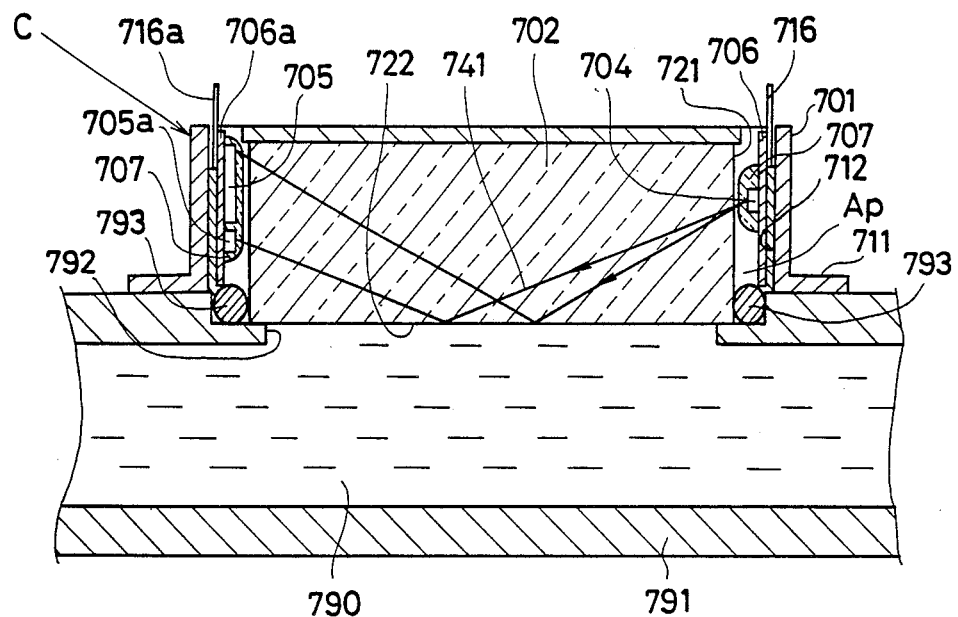
FIG. 1 is a cross sectional view of a mixing liquid ratio detector device according to first embodiment of the invention.

Now, first embodiment of the invention is described in reference to FIG. 1.

A detector device (C) is installed at an opening 792 provided with a pipe 791 through which a mixing liquid fuel 790 of gasoline and alcohol flows. The mixing liquid fuel 790 may be combination of gasoline with ethanol, butanol, methanol or other highly polymerized alcohol.

Otherwise, the combination may be alcohol and kerosene. Around the periphery of the opening 792, a cylindrical holder 701 is attached which has an upper lid at upper open end, and at the same time, having a flange 711 fixed to the pipe 791.

Figure 3:
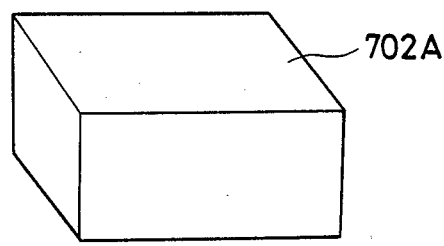
FIG. 3 is a perspective view of another modification form of column.

Into the holder 701, a glass column or plate 702 is liquid-tightly interfit by means of O-ring 793 with its outer bottom 722 contacting with the mixing liquid fuel 790. In this instance, the glass column 702 is brought into engagement with an inner side of the upper of the holder 701. The glass column 702 is made of flint glass having circular in perspective view as seen in FIG. 2, and having a refraction index of 1.55. The perspective view of the column may be of rectangle as seen at 702A in FIG. 3.

Between a circumferential outer wall 721 of the column 702 and an inner surface 712 of the holder 701, an annular space (Ap) is provided into which a base plates 706, 706a are located in opposed relationship with the column 702 interposed therebetween. The base plates 706, 706a has a photo diode 705 together with a compensation photo diode 705a and a light emitting diode 704 which in turn are coated with silicone resin 707. Both light emission area and light receiving area regarding to the three diodes 705, 705a, 704 are located in perpendicular relationship with a boundary in which the bottom 722 contacts with the mixing liquid fuel 790. The light emitting diode 704 is of Ga-As type, and emits infrared rays 741 when energized. The infrared rays 741 enter into circumferential wall of the column 702 through the annular space (Ap) to advance into an inner portion of the column 702. The rays 741 incident on the bottom 722 (boundary) at more than a critical angle totally reflect from the boundary and come out of the column 702 through the circumferential wall of the column 702.

The rays 741, thus coming out of the wall of the column 702, pass the annular space (Ap) to impinge on the photo diode 705 which produces an output according to the intensity of the rays 741 impinged on.

The amount of rays 741 impinged on the photo diode 705 changes in accordance with the critical angle at which the rays 741 reflect from the boundary 722, and changing the output from the photo diode 705. Change of the output allows to detect the mixing ratio of the fuel 790 to obtain the most appropriate ignition timing by means of a combustion control device equipped with automobile. Still member 716, 716a is a terminal electrodes for the output or an input.

With the structure thus far described, it is possible to provide a compact and endurable detector device (C) with low cost, but high detecting precision.

Figure 5:
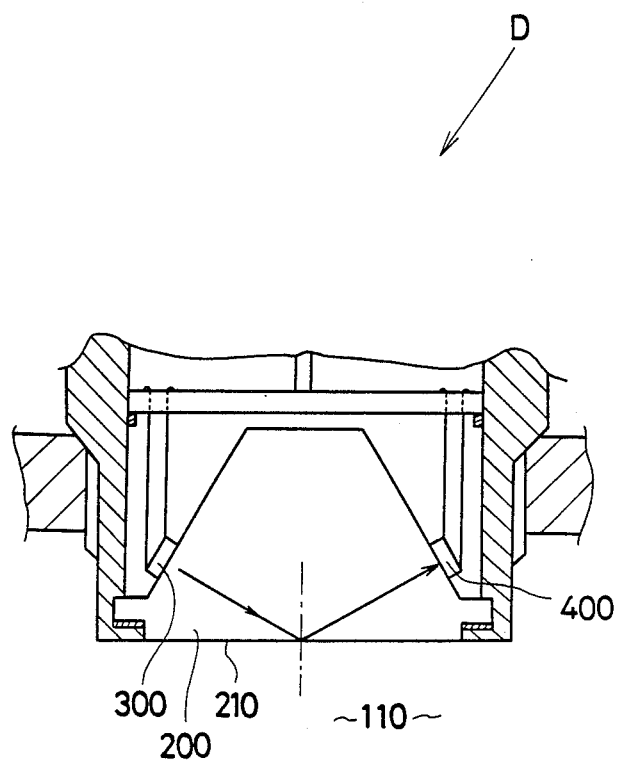
FIG. 5 is a view of a counterpart detector device.

To prove these effects, a counterpart device of FIG. 5a is cited to compare with a schematic view of FIG. 4 according to the first embodiment of the invention.

In FIG. 5a, dimensional relationship between ($l_1$), ($\theta$) and ($t_1$) is expressed as follows:

$l_1 = 2t_1 \tan \theta$, $l_1 = 3.46 t_1$ when incident angle ($\theta$) is 60 degrees. Where ($l_1$) represents a distance between the two diodes, while ($t_1$) represents a vertical distance between the boundary and the light emitting diode (photo diode).

The differential equation $dl_1/dt_1 = 3.46$ is obtained from the equation $l_1 = 3.46 t_1$.

Therefore, dimensional error of ($t_1$) affects on the dimension of ($l_1$) by the times of (3.46) which requires to make the light receiving area of the photo diode broad so as to absorb the dimensional error of ($t_1$).

In the meanwhile, the dimensional relationship $l_2 = D - t_2 \tan \theta / \tan \theta$ is obtained from geometrical calculation in FIG. 4, ($l_2$) = 0.557D − $t_2$ when incident angle ($\theta$) is 60 degrees.

Where (D) represents a distance between two diodes, while ($l_2$) and ($t_2$) in turn represent a distance between the photo diode and the boundary, and a distance between the light emitting diode and the boundary. It is understood that dimensional error of ($l_2$) influenced by the error of ($t_2$) and (D) remains less from the expression $l_2 = 0.557D - t_2$.

Light emitting area (light receiving area) of the light emitting diode (photo diode) is arranged in perpendicular relationship with the boundary, so that incident angle on the circumferential wall of the column becomes small (ex. 30 degrees) even when the critical angle incident on the boundary is somewhat greater (ex. 60 degrees).

The refraction angle (ex. 30 degrees) when the rays 741 comes out of the circumferential wall of the column, becomes small in the same case as identified above. This enables to eliminate the necessity of a transparent filler between the light emitting (photo diode) and the circumferential wall of the column.

It is noted that the column may be liquid-tightly sealed by means of a plate packing instead of O-ring.

In the opposite surface of the outer bottom 722, the upper surface of the column may have an undulating heat portion.

It is further noted that space between the light emitting diode and the circumferential wall may be filled with silicone or epoxy resin to prevent the surface of the diode from being fouled. In this instance, space between the photo diode and the circumferential wall may be filled with silicone or epoxy resin for the same purpose as identified above. This arrangement works to prevent the optical path from being significantly diverted even when the circumferential wall of the column is not so smooth.

Figure 6:
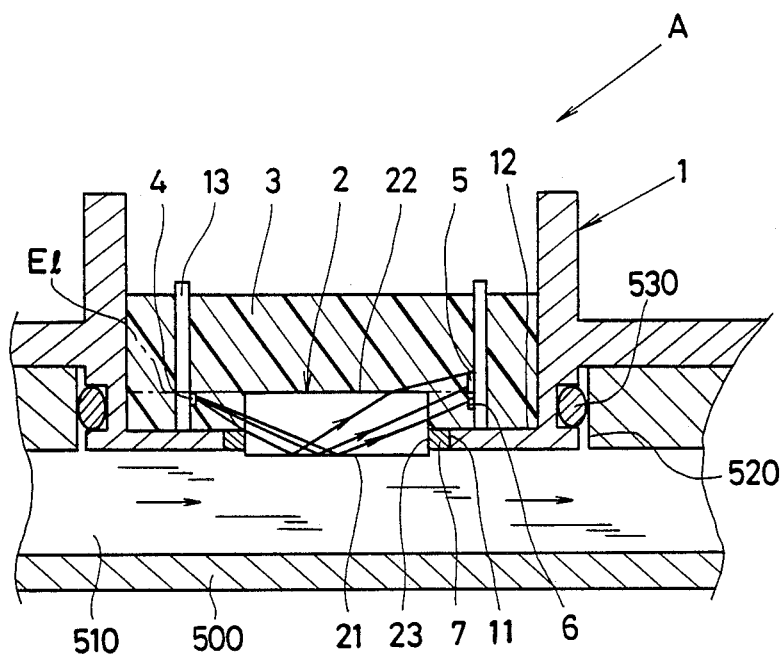
FIG. 6 is a cross sectional view of a mixing liquid ratio detector device according to second embodiment of the invention.

Referring to FIG. 6 in which a detector device (A) is shown as second embodiment which comprises a metallic holder 1 having a circular aperture 11 at its bottom. The device (A) further comprises a glass column 2 interfit into the aperture 11, a silicon-gel 3 supplied to the holder 1, and a light emitting diode 4, a photo diode 5 together with a compensation photo diode 6 each disposed in the silicone-gel 3. A glass ring 7 is provided to bond the glass column 2 to the holder 1 which is liquid-tightly secured to a pipe 500 by means of O-ring 530.

The device (A) is installed at the pipe 500 through an opening 520 in which a mixing liquid fuel of gasoline and alcohol 510 (refraction index: 1.33−1.43) flows. The holder 1 is made of stainless steel. An annular space is provided between a peripheral end of the aperture 11 and an outer surface of the glass column 2 for securing the glass ring 7. At an inner bottom 12 of the holder 1, a cylinder 13 of synthetic resin in fixedly placed to surround the glass column 2 which is made of flint glass (refraction index: 1.58), and measured 8 mm in diameter, and 2.5 mm in length (height).

The column 2 has an outer bottom 21 which is quite partly immersed in the mixing liquid fuel of gasoline and alcohol 510 to form a boundary 21, and at the same time, having an upper surface 22 located in opposite to the bottom 21, and a circumferential wall 23 around of which is surrounded by the glass ring 7.

The silicone-gel 3 serves as transparent filler and has a refraction index of 1.40 which is supplied to the holder 1 to the extend that the silicone-gel 3 approaches to an upper open end of the cylinder 13. A light emitting diode 4 (LED) is attached to an inner wall of the cylinder 13, vertical position of which falls somewhat below an extension line (E1) of the upper surface 22.

On the other hand, the photo diode 5 is attached to the inner wall of the cylinder 13 so as to oppose the light emitting diode 4 beyond the glass column 2 in a manner to straddle the extension line (E1).

The compensation photo diode 6 is installed at the inner wall of the cylinder 13 directly below the photo diode 5 in a manner to be located vertically lower than the extension line (E1).

The glass ring 7 is made of flint glass having height of 1 mm, and thickness of 1 mm. The melting point of the glass ring 7 is lower than that of the glass column 2. The glass ring 7 supports the glass column 2 to maintain the outer bottom (boundary) 21 to be partly immerse in the mixing liquid fuel of gasoline and alcohol 510.

Figure 2:
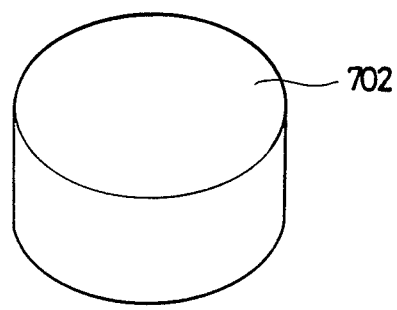
FIG. 2 is a perspective view of modification form of column.

An arrangement between height and diametrical dimension of the column 2, and vertical position of the photo diode 5 is determined such that light beams from the light emitting diode 4 enter into one side of the column 2 through the transparent liquid filler (silicone-gel) 3 to be incident on the boundary 21. The light beams incident on the boundary at an angle of more than a critical angle, totally reflect from the boundary 21, and advance through inner portion of the column 2 to come out partly form the other side of the column 2 as seen at an optical path 41 in FIG. 2, and partly coming out from an upper surface 22 of the column 2 through the silicone-gel 3 as seen at an optical path 42 to impinge on the photo diode 5 so as to produce an output according to the light beams impinged on.

It is noted that a vertical range as designated at 43 is a variable area, ranging from upper limit of alcohol component in the mixing liquid fuel 510 to lower limit alcohol component in the mixing liquid fuel 510. Change of the mixing ratio of the mixing liquid fuel 510 causes to increase the critical angle, so that passage of the light beams changes from the optical path 42 to the optical path 41 to diminish the vertical range 43.

Figure 8:
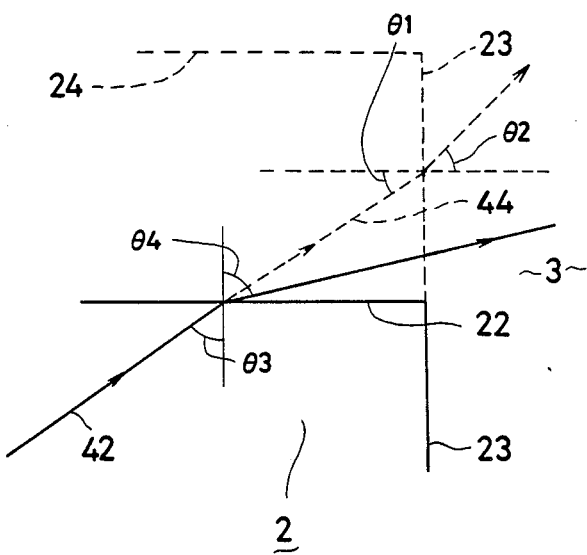
FIG. 8 is an explanatory view for showing how the light beams reflect at the side of the column.

In FIG. 8, how the optical refraction occurs at the upper surface 22 is depicted.

Since the refraction index of the glass column 2 is determined to be greater than that of the silicone-gel 3, the light beams form the light emitting diode 4 are as shown at solid-lined optical path 42 when the incident angle ($\theta 3$) is smaller than the refraction angle ($\theta 4$). When the light beams comes out of the circumferential wall 23 to enter the silicone-gel 3, relationship between the incident angle and the refraction angle is as expressed by an inequation $(\theta 1) < (\theta 2)$ as seen at broken lines 44.

Figure 7:
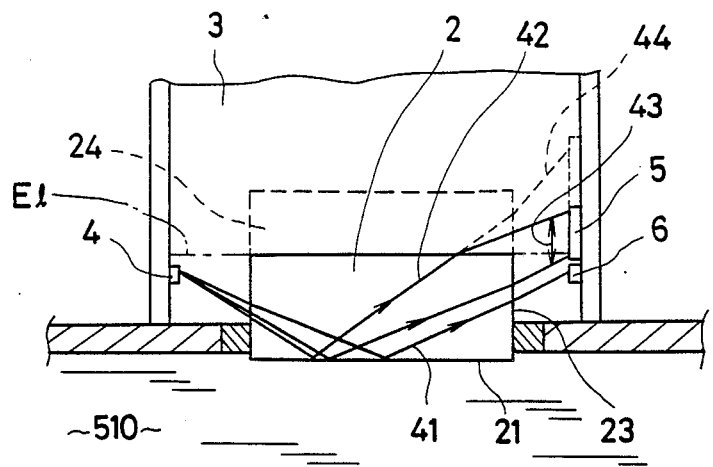
FIG. 7 is a cross sectional view of a detector device of FIG. 6 with optical path depicted.

In cases in which it is necessary for the light beams along the path 42 to let them come out of the wall 23 into the silicone-gel 3, the height of the column 2 is required to reach a level as seen at broken lines 24 in FIGS. 7 and 8.

The detector device according to the present invention has advantages as follows:

The glass column 2 is required at its scale dimension such as to include the one depicted by the solid line, thus making it possible to provide a compact and light weight detector device (A).

The light weight glass column 2 contributes to increase a bonding strength against the metallic holder 1.

The solid-lined optical path 42 makes it possible to prevent the light beams from broadly dispersing, thus enabling to make the light receiving area of the photo diode relatively small to lead to a compact diode with low cost.

This effect is all the more strengthened as the refractive difference between the silicone-gel 3 and the glass column 2 becomes greater.

It makes it possible to make the axial length dimension of the glass column 2 small so that the thermal stress from the glass ring 7 due to temperature change becomes minor so as to prevent cracks from occurring on the column 2.

Figure 9:
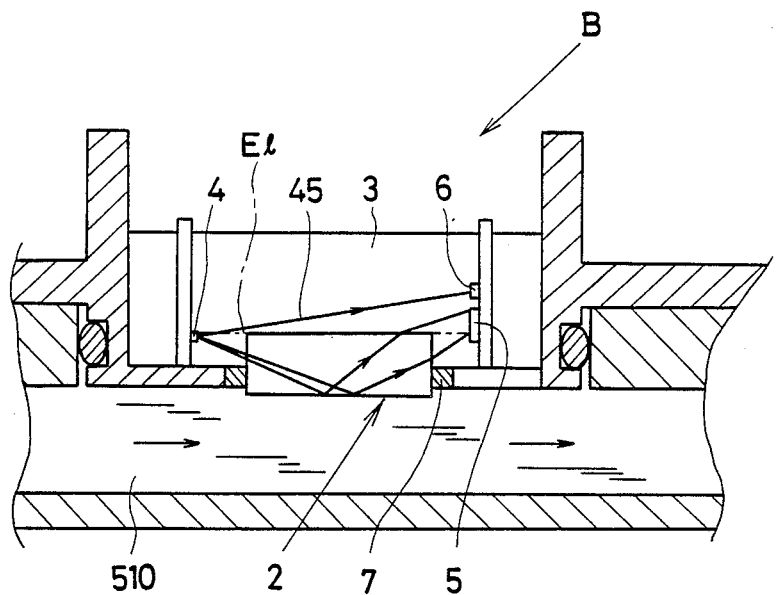
FIG. 9 is a view similar to FIG. 6 according to third embodiment of the invention.

FIG. 9 shows third embodiment of the invention. In a detector device (B) according to this embodiment, the compensation photo diode 6 is located somewhat above the photo diode 5. The light beams from the light emitting diode directly passes through the silicone-gel 3 to impinge on the photo diode 5 without advancing into the glass column 2 as seen at an optical path 45. This arrangement enables to normally monitor the light intensity of the light emitting diode regardless of whether the mixing ratio of gasoline and alcohol changes.

Further, this arrangement enables to prevent the light beams 45 from being occluded by the glass ring 7. The arrangement of the compensation photo diode 6 is substantially immune to a critical angle depending on the mixing ratio of gasoline and alcohol 510, thus positioning the compensation photo diode 6 with ease.

It is appreciated that the mixing liquid to be detected may be of mobile or stationary type.

Further, it is noted that a transparent plate may be of property which resists erosion of the mixing liquid to be detected such as sodium glass, Pyrex glass, borosilicate glass or acryl synthetic resin.

Furthermore, it is noted that the glass column plate may be of polygon or ellipse.

It is also appreciated that a critical angle incident on the boundary may preferably be determined to be more than 45 degrees from the view point of ready installation of the light emitting diode and the photo diode.

While the invention has been described with reference to the specific embodiment, it is understood that this description is not to be construed in a limiting sense in as much as various modifications and additions to the specific embodiment may be made by skilled artisan without departing from the spirit and scope of the invention.

What is claimed is:

1. A mixing liquid ratio detector device comprising;
an optically permeable column, a bottom surface of which is brought in contact with a mixing liquid composed of at least two components, and forming a boundary between the mixing liquid and the bottom surface which is brought in contact with a mixing liquid;
a light emitting element located to face to one side of the optically permeable column;
a light receiving element located in the opposite relationship with the light emitting element in a manner to face to another side of the column with the column interposed therebetween;
light receiving area of the light receiving element and light emitting area of the light emitting element being each arranged in the neighborhood of the column in generally perpendicular relationship with the boundary between the mixing liquid and the column, such that light beams from the light emitting element enter the boundary through one side of the column, the light beams incident on the boundary at an angle more than a critical angle being totally reflected from the boundary, and advancing through an inner portion of the column to come out from the other side of the column, and impinging on the light receiving element so as to produce an output according to the intensity of the light beams impinged thereon.

2. A mixing liquid ratio detector device comprising;
an optically permeable column, a bottom surface of which is brought in contact with a mixing liquid composed of at least two components, and forming a boundary between the bottom surface and the mixing liquid;
a holder disposed for supporting the optically permeable column;
a light emitting element located to face to one side of the optically permeable column;
a light receiving element located in the opposite relationship with the light emitting element to sandwich the column therebetween;
a transparent liquid filler disposed to fill between the light emitting element and the column, and at the same time, filing between the light receiving element and the column;
an arrangement between height and diametrical dimension of the column, and vertical position of the light receiving element being determined such that light beams from the light emitting element enter into one side of the column through the transparent liquid filler to be incident on the boundary, the light beams incident on the boundary at an angle more than a critical angle totally reflecting from the boundary to advance through inner portion of the column so as to come out partly from the other side of the column, and partly coming out from an upper surface of the column to impinge on the light receiving element so as to produce an output according to the intensity of the light beams imPinged thereon.

3. In a mixing liquid ratio detector device as recited in claim 2, the transparent liquid filler is smaller than the column in refraction index, while all the light beams incident on the boundary at more than a critical angle are adapted to come out from the other side of the column.

* * * * *